(12) United States Patent
Lidén et al.

(10) Patent No.: US 6,520,000 B2
(45) Date of Patent: Feb. 18, 2003

(54) METHOD AND DEVICE FOR ABRASION DETERMINATION

(75) Inventors: Jenny Lidén, Halmstad (SE); Tomas Nilsson, Halmstad (SE); Camilla Palmertz, Västra Frölunda (SE)

(73) Assignee: Volvo Car Corporation, Göteborg (SE)

(*) Notice: Subject to any disclaimer, the term of this patent is extended or adjusted under 35 U.S.C. 154(b) by 0 days.

(21) Appl. No.: 09/683,220

(22) Filed: Dec. 3, 2001

(65) Prior Publication Data

US 2002/0069690 A1 Jun. 13, 2002

Related U.S. Application Data

(63) Continuation of application No. PCT/SE00/01129, filed on May 31, 2000.

(51) Int. Cl.⁷ .................................. G01B 15/00
(52) U.S. Cl. ............................................... 73/7
(58) Field of Search ................. 73/7, 866.4, 866.5, 73/86; 116/208

(56) References Cited

U.S. PATENT DOCUMENTS 5,388,331 A * 2/1995 Siamak ..................... 116/208
5,648,915 A   7/1997 McKinney et al.
5,947,053 A * 9/1999 Burnham et al. ........... 116/208

FOREIGN PATENT DOCUMENTS

| DE | 2448784 | | 4/1975 | |
| EP | 0499215 A3 | | 8/1992 | |
| GB | 448223 | * | 6/1936 | ............... 116/208 |
| GB | 2137080 | * | 10/1984 | ............... 116/208 |
| JP | 60177243 | | 9/1985 | |
| SU | 1596228 | | 9/1999 | |

* cited by examiner

Primary Examiner—Robert Raevis
(74) Attorney, Agent, or Firm—Howrey Simon Arnold & White LLP

(57) ABSTRACT

A method and device for determining abrasive forces is disclosed. In order to determine the forces, at least two removable and distinguishable layers are applied on top of each other to a substrate or base so as to cover one another. Each layer requires a predetermined abrasive force for penetrating and removing the layer by scraping. The strength or force that is required is smaller the closer to the surface the layer is positioned. When the layers are subjected to abrasive forces, parts of the applied layers are scraped off, starting from the outermost layer and further downwards into the underlying layers. In this manner, one of the layers is exposed at each point, thereby indicating the abrasive force at that point. The exposed surface of each layer may then be identified. The method and device are particularly suitable in car-crash testing in order to assess the abrasive forces arising from airbags.

26 Claims, 4 Drawing Sheets

METHOD AND DEVICE FOR ABRASION DETERMINATION

CROSS REFERENCE TO RELATED APPLICATIONS

The present application is a continuation of International Application No. PCT/SE00/01129, filed May 31, 2000, which claims priority to Swedish Application No. 9902075-2, filed Jun. 3, 1999.

BACKGROUND OF INVENTION

1. Technical Field

The present invention relates to a method and device for abrasion determination on a surface subjected to abrasive forces. More specifically, the invention relates to a method and device for determining abrasions on a substrate having at least two distinguishable superimposed layers that covered each other. Even more particularly, the invention relates to such a method and device for assessment of the abrasive forces to which an individual is exposed upon impact against an airbag during inflation of the airbag or against interior surfaces.

2. Background Information

Contact between two surfaces causes various types of effects that may be harmful to at least the more sensitive one of the two surfaces. Examples of such effects include pressure, friction and abrasive forces.

Reference to abrasive forces herein should be understood to refer to the forces that occur when an uneven surface slides against another surface under pressure, such as sandpaper against a piece of wood. Another example is human skin sliding against rough surfaces, such as asphalt paving or coarse textiles. The furrows that the scraping or abrasion causes on the human skin may result in injuries with consequential bleeding and scarring.

Abrasive forces may be of different types. For example, the contact surface may vary in coarseness and/or be applied with varying pressure. The coarser the surfaces and/or higher pressures, the more severe the abrasions. The more severe the abrasive forces, the higher the risks of abrasion-induced injuries and, as a consequence, of scarring.

While several methods have been developed for measuring pressure-induced damages, there still exists no satisfactory method for accurately assessing the abrasive forces that arise, for example, to the human skin in situations as described above. For example, the cloth of an airbag brought into contact with a person's skin inside the car can cause abrasion injuries. The contact surface of the airbag varies according to its stage of inflation. In other words, it is important to study the detrimental effects that an airbag may have on the human skin in order to determine any abrasive forces. By doing so, airbags that cause as little abrasion as possible upon contact with the human skin can be developed.

In one method used for determining whether two surfaces come into contact with one another in vehicle crash tests, exposed body parts, such as the arms and the face of a crash-test dummy, are covered with a coating of paint. The coating can vary from a simple coating of lipstick to a more complex solution of pigments mixed with a hardener for suitable hardness. However, the information gained from these tests is limited. With this method, it is possible to only determine whether the two surfaces have been in contact with one another or not.

Another problem with the above method occurs in spraying the pigment solution onto the crash-test dummy. By spraying on the coating, it is difficult to obtain an evenly thick coating throughout. An even coating is necessary in order to obtain a comparable indication across the entire relevant area.

German Patent Specification DE 24 48 784 A1 describes a method and device for examining the configuration of a glass slab along its outer periphery. The inspection is performed by placing the slab in a check frame. Along a comparatively narrow section of the glass slab corresponding to its outer periphery, several layers of paper having different colors are applied, one on top of the other. As the glass slab is placed inside the frame, the slab, should its shape not coincide with that of the frame, scrapes off the paper layers where the slab configuration does not agree with that of the frame. Depending on where and how much the layers are scraped off, it is possible to evaluate the configuration of the glass slab.

SU 1596228 describes a technique in which the rotating cutting tools of an earth milling machine are coated with several layers of paint in order to determine which sections of the tool are most exposed to wear. In this case, scraping off the paint occurs gradually in the same place as the cutting tools are rotated, i.e., the larger the number of rotations, the more severe the scraping effects. However, the results of this technique only indicate that a certain spot on the cutting tool has a greater exposure to more scraping or wear damage than another spot.

Japanese Patent No. 60-177243 describes a device and method for discovering irregular wear on vehicle tires. As indicated in the Abstract, part of the tire is coated with several differently colored layers of rubber. In this case the scraping-off is gradual on those places having the greatest exposure to scraping effects as the tire is rotating, i.e., the larger the number of rotations, the more severe the scraping effects. Still, the results only indicate that one spot on the tire is more exposed to scraping damage than another spot.

In view of the above, there is a need for a method that allows a more precise assessment of the severity and extent of abrasive forces, such as those which a person may be exposed to upon impact with an inflated airbag, or against other interior surfaces of a vehicle. Further, there is a need for a device for implementing the method that is as simple as possible while at the same allowing a precise assessment of the abrasion.

SUMMARY OF INVENTION

The present invention provides a method and device for determining the abrasion or amount thereof on a surface subjected to abrasive forces. According to the invention, at least two distinguishable superimposed layers cover each other over a base or substrate. The layers are removable by scraping. An abrasion is measured by subjecting the layer-coated substrate to abrasive forces, which is followed by reading the degree of penetration through one or more of the distinguishable layers. Each layer is calibrated to correspond to a predetermined amount of abrasive force upon penetration of the respective layer. This is accomplished by varying the adhesion to the layer or substrate underneath. Further, the abrasive force required to scrape off a certain layer decreases the further from the substrate that the layer is located.

In one embodiment, the thickness of each individual layer decreases the further from the substrate that the layer is located. As a consequence, the adhesion of the layers decreases accordingly.

In one embodiment, the method of the present invention involves reading and assessing the location of the penetration on the substrate and/or the size of the scraped off area on the respective area.

In one embodiment, the layers have different reactants and/or crystalline properties. The layers may also have different reflection coefficients. In doing so, the various layers can react differently to radiation such that the area exposed to abrasive force can be radiated in order to identify areas exposed to abrasive force of different strength and/or different colors and or different patterns.

The method according to the invention involves the steps of applying on a substrate two or more distinguishable superposed layers that cover each other. These layers may be scraped off. The measurement of abrasion is determined by exposing the substrate with the layers applied thereon to abrasive forces. This is followed by reading the degree of penetration, if any, through one or several of the different layers, and assessing the extent of the abrasive forces. Each layer is calibrated to correspond to a premeasure of abrasive force required to penetrate the respective layer, by varying the layer's ability of adhering to the layer or substrate underneath, the calibration being such that the measure of abrasive force required to scrape off a certain layer decreases the closer to the free surface that the layer is located.

One advantage of the invention is that it offers the ability to simulate the effect of abrasive forces on complex surfaces, such as human skin, in a more precise manner.

By applying several layers that are distinguishable from one another on the substrate, it is possible to determine the strength of the abrasive force within predetermined intervals. In other words, in order to scrape off the first layer, an abrasive force of a prestrength is required. A stronger abrasive force can be required to simultaneously scrape off the next layer underneath, and so forth. The layer that becomes exposed within an area subjected to abrasive forces thus indicates the strength of the abrasive force.

In accordance with one embodiment of the invention, the thickness of the individual layers differs. For example, the closer the layer is located to the surface the thinner the layer. By so doing, the adhering force of the layers thus is reduced.

In accordance with another embodiment of the invention, not only is the strength of the penetrating abrasive force assessed, but also the place of penetration on the surface subjected to the abrasive force. As such, the invention provides a picture of the location of the abrasive forces, or where the abrasive forces are occurring.

In another embodiment of the invention, the extent or area of scraped-off sections on each respective layer is assessed. This assessment provides a picture of the extent of the abrasive forces.

In a further embodiment of the invention, both the position and the extent on the surface subjected to abrasion are determined.

It should be noted that on those spots where several layers are scraped off, this process takes place in one single scraping motion. Thus, it is not a situation involving a gradual scraping off action with one layer at a time being scraped off. Instead, the present invention is directed towards determining the instantaneous strength of the abrasive force and, in accordance with the various embodiments such as mentioned above, also the extent and/or location thereof.

In accordance with a preferred further development of the inventive method, the distinguishing feature may be visual. For example, the individual layers can be differently patterned and/or colored. This feature can also be invisible to the eye. For example, the distinguishing feature can be achieved by using different reactants to radiation (such as UV radiation) in the various layers. The reaction to the radiation varies in a measurable way so that the section subjected to abrasive forces can be radiated in order to identify the areas exposed to abrasive force of different strength. In other embodiments, the individual layers could also have different crystalline properties and/or reflection coefficients.

In accordance with another embodiment of the invention, the identification of the uncovered parts of the respective layer is preferably made by scanning the entire section digitally and thereafter data processing the section in a suitable manner. An identification method of this is described in European Patent No. 442699. In this case, the scanned object is conventionally radiated by a beam of light. The two-dimensional image information is then picked up with the aid of a sensor device. The sensor device reproduces the scanned object and converts the light image to electrical signals.

In accordance with another embodiment of the invention, the layers can be subjected to an abrasive force, for example, contact with an expanding air bag. Tests of this nature by means of a prototype of the inventive object have resulted in the pattern shown in FIG. 3, discussed hereinafter. The pattern clearly shows marks due to the airbag seams. As indicated, these seams cause more severe abrasion injuries than the smoother sections of the airbag.

In accordance with another embodiment of the invention, the layers are applied on a crash-test dummy that is subjected to a vehicle collision. The dummy, coated in accordance with the teachings of the invention, then provides information as to the potential location and extent of the abrasion to an individual in a collision. This information, together with other information such as the video recordings of the crash process, indicates which interior surfaces inside the vehicle cause abrasion injuries. In addition, it is possible to coat the interior surfaces of the vehicle with layers in accordance with the teachings of the invention, in order to obtain information as to which surfaces are hit and cause abrasion.

Advantages of the invention include being able to obtain clear information as to within which intervals the strength of the abrasive force resides. At the same time, it becomes possible to assess the location and the extent of the abrasion. Another advantage provided by the invention is that it is simple to use.

As indicated above, the invention includes a substrate onto which at least two layers that are distinguishable from each other are applied. The layers are preferably removable by scraping. The layers are applied one on top of and covering the other. Each layer is calibrated with respect to its different ability to adhere to the layer underneath or to the substrate. As such, it corresponds to a predetermined measure or strength of scraping force at which the respective layer is penetrated. The measure or strength necessary to scrape off a certain layer diminishes the closer to the free surface that the layer is located.

The invention offers the possibility to more precisely simulate complex surfaces such as human skin. This makes it possible to assess the abrasion. At the same time, the inventive device is simple to manufacture and to use.

According to one embodiment of the inventive device, the thickness of the individual layers differ. Preferably, the thickness of the layers decreases the closer to the surface that the layer is positioned. In doing so, the resistance against abrasion also differs. The variable resistance against abrasion that the individual layers possess is essential to the method and to the device in accordance with the invention. In accordance with another embodiment of the inventive device, the layers are applied a sheet made from a suitable material. A device of this kind is useful in the implementation of the method according to the invention. A sheet of a non-stretchable material is easy to apply on surface comprising a single curve whereas a sheet of a stretchable material, such as plastic foil, could be applied on surfaces comprising double curves or having a more complex configuration.

The sheets can consist of a plastic material. Preferably, the material is a plastic foil. Due to the higher pliability of the material and its stronger tendency to withstand elongation and stress, this embodiment is more suitable for surfaces comprising double curves or having a more complex configuration, such as in the face of a crash-test dummy.

An advantage of this device is that it may be manufactured under suitable and controllable conditions. This guarantees that the layers possess the desired properties and eliminates the inconvenience of having to apply the layers directly on a substrate such as a test dummy, making it possible to use presheets.

According to another embodiment of the inventive device, the individual layers may include at least one scrape off coat and one top coat, the surface of the latter layer being harder than that of the scrape-off coat. In this case, the thickness of the top coats may decrease as seen from the substrate upwards. Accordingly, weaker abrasive force are required to penetrate a topcoat located closer to the surface. It is also possible to vary the ability to adhere. The adhesion against any one underlying layer that a layer composed of a top coat and a scrape off coat possesses is determined by the adhesion between the top coat and the scrape off coat underneath, i.e., in the layer. Briefly speaking, it is the top that determines the resistance against abrasion in the type of layer.

Additional advantageous embodiments of the invention will become apparent from the following description of the invention.

It may be desirable to adapt the adhesion of the individual layers to predetermined abrasive force levels for the purpose of simulating as best possible the properties of human skin, and to easily obtain interpretable indicia of abrasion. One possibility in this regard is to use the damage codes of the ARS system (Abrasion Rating System) described in "Airbag-Induced Skin Abrasions: Design Factors and Injury Mechanisms' by Reed, Schneider and Burney, University of Michigan, 1992, set forth in the table below.

By adapting the properties of the layers as exemplified below, tests show that it is possible to relate each layer to a predetermined ARS level, thus facilitating the subsequent interpretation of the effects of abrasion.

Table 1: ARS System Levels
ARS
Level Description of damage

1) Abrasion not sufficiently severe to cause bleeding or flow of fluids 24 hours or less after the accident. Erythema or brief discoloration of skin.

2) Bleeding, dripping fluids or formation of crust at the earliest after 30 minutes but within 24 hours of the accident.

3) Superficial, incomplete abrasion lesion on the skin, characterized as lesion on the upper layer of dermis and fine spot-like bleeding from the vessels.

4) Deep, incomplete abrasion lesion characterized as lesion on the lower dermis layer with more extensive spot bleeding.

5) Complete abrasion lesion throughout the entire dermis and into the subcutaneous tissue.

BRIEF DESCRIPTION OF DRAWINGS

The present invention will be described in more detail in the following with reference to the accompanying drawings, wherein.

DETAILED DESCRIPTION

Figure 1:
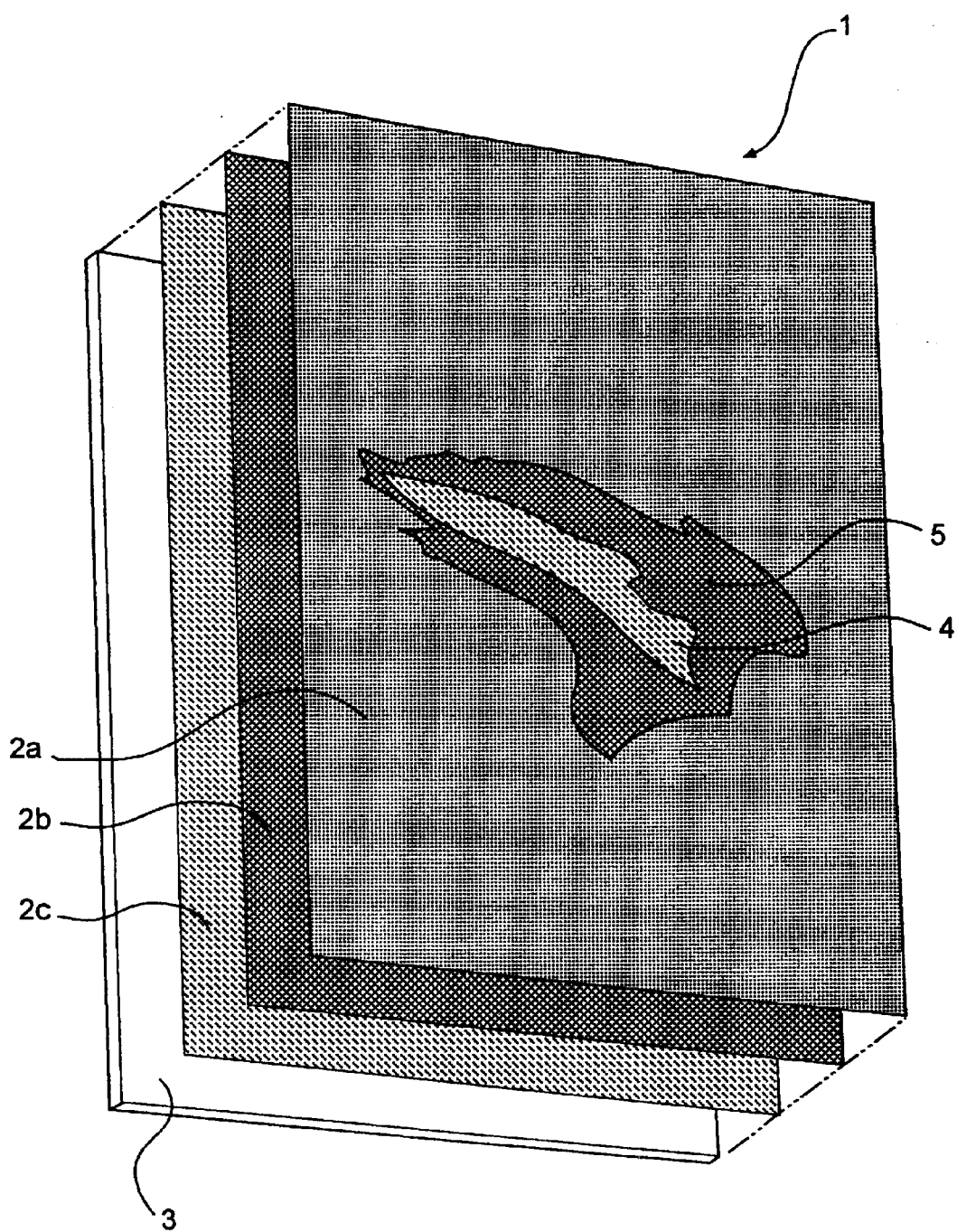
FIG. 1 is a exploded schematic view of one embodiment of a device according to the invention.

FIG. 1 shows a device 1 in accordance with one embodiment of the invention. The device includes several layers. As illustrated, three layers 2a, 2b, 2c are applied to a substrate 3. However, it should be understood that the invention is not limited to three layer. The layers can include various materials, such as a sheet of paper or plastic foil. According to the drawing, one area 4, 5 has been exposed to abrasive force.

In accordance with one embodiment, each layer 2a, 2b, 2c is formed by two coats such as one colored coat of a scrape off paste and a harder top coat of a UV varnish. This type of layer composition is commonly used on scrape off or scratch lottery tickets.

In contrast to scrape off lottery tickets, the device according to the invention includes two or more layers 2a, 2b, 2c. The top coat of an underlying layer 2b and 2c, respectively, must be the carrier of the scrape off coat of the neighboring layers 2a and 2b, respectively. The properties of the top coat and the scrape off coat, such as thickness, hardness, porosity, surface texture and so on, determine the inter-layer adhesion and, consequently, the strength of the abrasive force required to scrape off layer from the layer immediately below. Preferably, the adhesion is reduced for each layer applied to the substrate, i.e., the strength of the adhesion between two layers is lower the further the distance from the substrate. The reason for this is to ensure that the number of layers scraped off indicate the strength of the abrasive force. The top layer 2a, which is the one furthest away from the substrate, should be easier to scrape off than the immediately following layer 2b, which in turn is easier to scrape off than the immediately following layer 2c, and so forth.

Preferably, the top-coat closest to the substrate 3 is made relatively thick whereas the top-coats subsequently applied decrease in thickness. As a thick top-coat of varnish is more difficult to penetrate than a thin one, the arrangement makes it possible to differentiate between required abrasive force independent of the depth position of the layers.

According to another preferred embodiment the uppermost scrape off coat 2a is entirely without a top coat in order to further reduce the strength of abrasive force required to scrape off the uppermost colored layer.

The layers shown in FIG. 1 have been subjected to abrasive force of varying strength. In a centrally located area 4, the abrasive force has scraped off two layers 2a, 2b, thus uncovering or exposing the third layer 2c. In another area 5, surrounding area 4, only the uppermost layer 2a is scraped off, uncovering only the second layer 2b. The abrasive force that may have affected the device beyond area 5 is too weak to scrape off even the uppermost layer 2a.

Figure 2A:
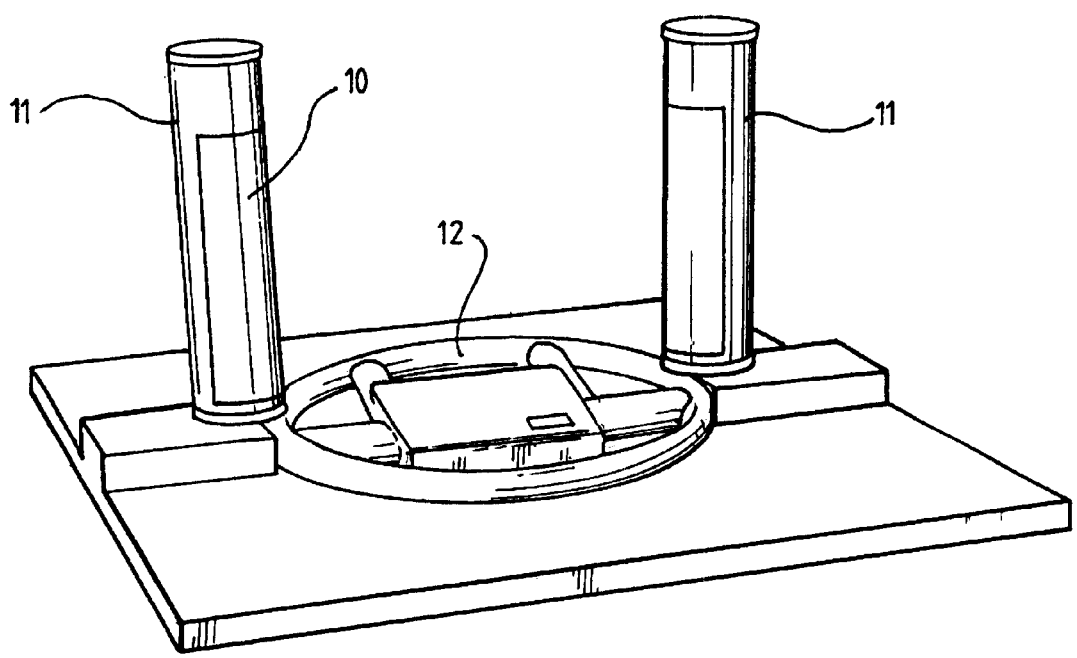
FIG. 2a illustrates a perspective view of a testing rig for determining the abrasion from an airbag on the arms of the driver.
Figure 2B:
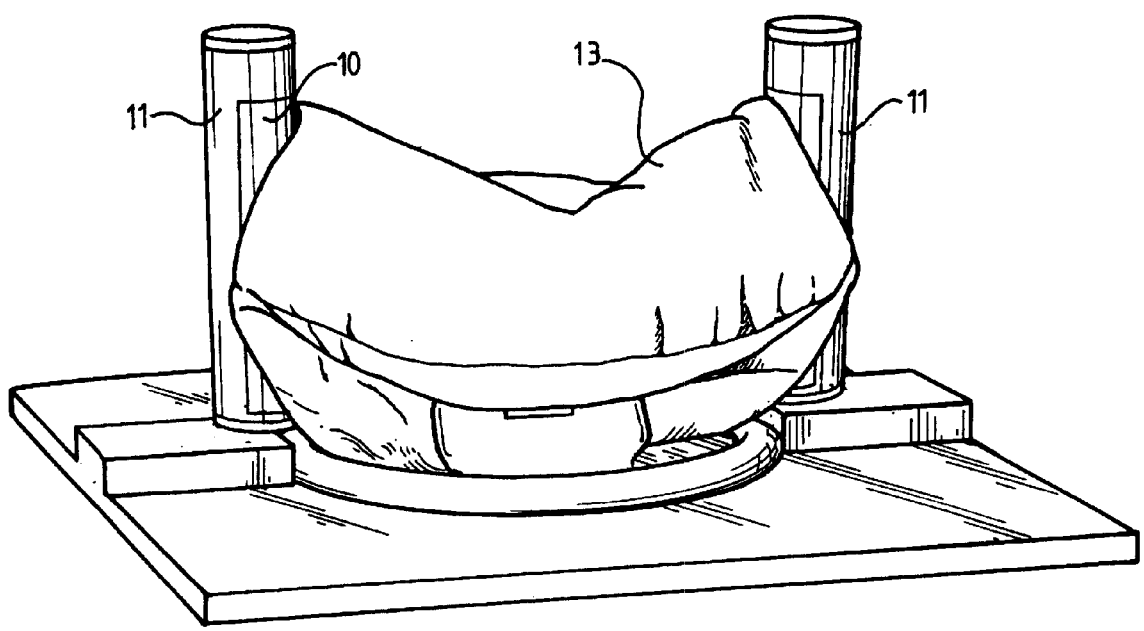
FIG. 2b illustrates a perspective view of a testing rig as in FIG. 2a while the test is in progress.

One application of the method and device according to the invention is in connection with testing vehicle airbags as shown in FIGS. 2a-2b. In the testing rig shown, the inventive device is applied in the form of sheets 10 comprising four differently colored abrasion-removable layers on cylinders 11 representing the arms of the driver. Between the cylinders, there is arranged a steering wheel 12 with an airbag 13 mounted thereon. The airbag is made to expand, with the expansion bringing the sheets 10 into contact with the face of the airbag (FIG. 2b). In this manner, the sheets are exposed to an abrasive force of varying strength. The abrasive force makes a pattern on the sheets. The pattern includes the colors of the individual layers. The areas where the deepest layer is visible correspond to the areas exposed the strongest abrasive force, and so forth.

Figure 3:
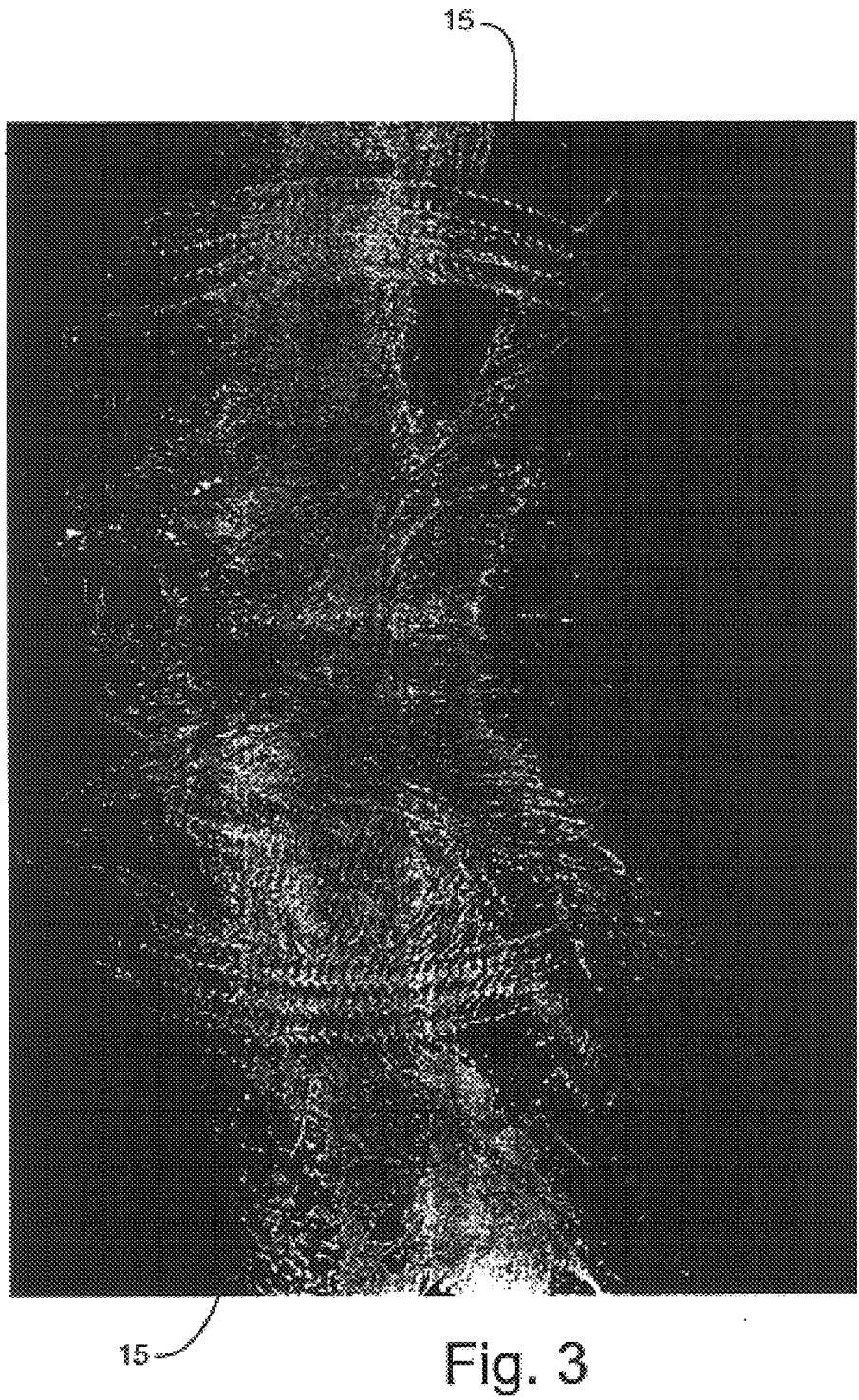
FIG. 3 illustrates the results from a test carried out on a testing rig as shown in FIGS. 2a and 2b.

In an alternative configuration not illustrated, a cylinder representing the head of a driver could be arranged above the steering wheel in FIG. 2. The results of such a test is shown in FIG. 3. Although this black-and-white reproduction of the layers does not reveal their different colors, it still clearly shows that the seams 15 of the airbag have caused violent abrasions.

When crash-test dummies are used, sheets according to the invention can be applied in suitable places on the dummy prior to the test. In the case of surfaces comprising a double curve or having a more complex configuration, it may be more suitable to use small pieces of a sheet according to the invention. The sheet can be made from a stretchable material, such as a foil material, making its application to any surface easier. In this case, the abrasion removable layers must possess properties that ensure that they are not damaged by the effects of elongation and other stress that may arise in the sheet.

The plastic material, such as a plastic foil, is a material that is more resistant to any elongation and stress that may arise when a sheet is folded or bent. Alternatively, the sheet may be replaced by a abrasion-removable layer of plastic foil, i.e., several distinguishable abrasion-removable plastic-foil layers are arranged on top of one another so as to cover each other in the same manner as the scrape-off paste and the UV varnish. These layers are then advantageously applied directly on optional surfaces of a comparatively more sinuous or complex configuration. For example, the surfaces may be the complex shapes of the face of the crash-test dummy. The plastics material must not be too tough, since a scraped-off layer, if too tough, can resume its original shape, i.e., the inherent resilience of the material tends to cause the abrasion sore to "heal". The area of the scraped layer then becomes more difficult to assess. For example, a plastic layer, if too resilient, results in a higher degree of uncertainty of measurement.

Instead of coloring the individual layers for purposes of distinguishing between them, it is possible to use different layers having individual patterns, such as patterns of lines, or dots of various kinds.

One embodiment of the invention might involve applying a top coat such as a UV varnish on the uppermost scrape off coat only, i.e., on the coat furthest away from the substrate. One advantage of applying a top coat on at least the uppermost or only the uppermost scrape-off coat is that the layers will have a higher degree of protection against unintentional abrasion that may arise, for example, due to careless handling of the sheets.

It is likewise possible to use different materials for each layer to construct the device according to the invention. For example, scrape off paste or UV varnish in different combinations may be applied on a scrape off, plastic foil layer.

Generally speaking, the invention may be used in a large variety of other fields of application in addition to its use in crash tests. For example, the invention may be used in material testing for determining the properties of the material when exposed to abrasive force. The invention can also be used to choose suitable wall-covering materials in premises where people risk coming into rough contact with walls and floors, such as in sports halls.

While there has been disclosed effective and efficient embodiments of the invention using specific terms, it should be well understood that the invention is not limited to such embodiments as there might be changes made in the arrangement, disposition, and form of the parts without departing from the principle of the present invention as comprehended within the scope of the accompanying claims.

What is claimed is:

1. A method of determining abrasion on a surface subjected to abrasive forces, the method comprising the steps of:
   providing a substrate with at least two distinguishable superposed layers covering each other, said layers being removable by scraping;
   characterized in that the measurement of the abrasion is effected by exposing the layer-coated substrate to abrasive forces;
   reading the degree of penetration, if any, through at least one of the different layers;
   wherein each layer is calibrated to correspond to a predetermined measure of abrasive force upon penetration of the respective layer by varying the adhesion to the layer or substrate underneath; and
   wherein the abrasive force required to scrape off a certain layer decreases the further from the substrate said layer is located.

2. The method as claimed in claim 1, wherein the thickness of each individual layer decreases the further from the substrate said layer is located and, consequently, the adhesion of the layers decreases.

3. The method as claimed in claim 1, wherein the location of the penetration on the substrate and/or the size of the scraped-off area on the respective layer is/are read and assessed.

4. The method as claimed in claim 1, wherein the layers have different reactants and/or different crystalline properties and/or different reflection coefficients, the different layers reacting differently to radiation, whereby the area exposed to abrasive force may be radiated in order to identify areas exposed to abrasive force of different strength, and/or different colors, and/or different patterns.

5. The method as claimed in claim 1, wherein the step of reading penetration, if any, and of assessing the actual abrasion, is effected by reproducing electronically and thereafter identifying and locating by means of data processing the parts of the surface uncovered as a result of abrasion.

6. The method as claimed in claim 1, wherein the step of subjecting the layers to abrasive force further comprises the step of bringing the layers into contact with an expanding airbag.

7. The method as claimed in claim 1, further comprising the step of applying the layers on a crash-test dummy and/or other interior surfaces in a vehicle, in order to assess the abrasive forces arising from a vehicle crash.

8. A device for determination of abrasion to a surface subjected to abrasive forces, the device comprising:

at least two distinguishable superimposed layers covering each other, said layers being removable by scraping;

a substrate for the at least two layers;

wherein each layer is calibrated to correspond to a predetermined measure of abrasive force upon penetration of the respective layer by varying the adhesion to the underlying layer or substrate; and wherein the measure of the abrasive force required to scrape off a certain layer decreases the closer to the surface that said layer is located.

9. The device as claimed in claim 8, wherein the thickness of the layers decreases as calculated from the substrate.

10. The device as claimed in claim 8, wherein each layer is calibrated to correspond to a certain type of injury or level of injury to the human skin.

11. The device as claimed in claim 8, wherein the substrate is a sheet of paper.

12. The device as claimed in claim 8, wherein the substrate is a crash-test dummy.

13. The device as claimed in claim 8, wherein the substrate is an interior surface in a vehicle.

14. The device as claimed in claim 8, wherein the layers have different colors and/or patterns and/or reactants and/or different crystalline properties and/or different reflection coefficients.

15. The device as claimed in claim 8, wherein at least one layer comprises a scrape off coat and a top coat, said top coat having a harder surface than the scrape off coat.

16. The device as claimed in claim 15, wherein all layers comprises a scrape off coat and a top coat, said top coat having a harder surface that the scrape off coat.

17. The device as claimed in claim 15, wherein the thickness of the top coat decreases as calculated from the substrate.

18. The device as claimed in claim 15, wherein the uppermost scrape off coat is entirely without a top coat.

19. The device as claimed in claim 15, wherein only the outermost layer consists of a scrape off coat and a top coat and the underlying layers consist of a scrape off coat only.

20. The device as claimed in claim 15, wherein the scrape off coat consists of a colored scrape off paste and the top coat of varnish.

21. The device as claimed in claim 20, wherein the varnish is a UV varnish.

22. The device as claimed in claim 8, wherein the various layers are comprised of a plastics material.

23. The device as claimed in claim 22, wherein the plastics material is plastic foil.

24. The device as claimed in claim 8, wherein different materials are used for each respective layer.

25. The device as claimed in claim 24, wherein the different materials are selected from the group consisting of plastic foil, a UV varnish and a scrape off paste.

26. The device as claimed in claim 8, wherein the various layers are comprised of plastic foil, a UV varnish and a scrape off paste.

* * * * *